(12) United States Patent
Frobisher (10) Patent No.: US 10,842,196 B2
(45) Date of Patent: Nov. 24, 2020

(54) ARTICLE AND APPARATUS FOR GENERATING AN AEROSOL

(71) Applicant: BRITISH AMERICAN TOBACCO (INVESTMENTS) LIMITED, London (GB)

(72) Inventor: Paul Frobisher, London (GB)

(73) Assignee: BRITISH AMERICAN TOBACCO (INVESTMENTS) LIMITED, London (GB)

(*) Notice: Subject to any disclaimer, the term of this patent is extended or adjusted under 35 U.S.C. 154(b) by 151 days.

(21) Appl. No.: 15/574,233

(22) PCT Filed: May 12, 2016

(86) PCT No.: PCT/EP2016/060752
§ 371 (c)(1),
(2) Date: Nov. 15, 2017

(87) PCT Pub. No.: WO2016/184783
PCT Pub. Date: Nov. 24, 2016

(65) Prior Publication Data
US 2018/0098577 A1   Apr. 12, 2018

(30) Foreign Application Priority Data
May 15, 2015   (GB) .................................. 1508405.6

(51) Int. Cl.
*A24F 47/00*   (2020.01)
*A61M 15/06*   (2006.01)
(Continued)

(52) U.S. Cl.
CPC ......... *A24F 47/008* (2013.01); *A61M 11/041* (2013.01); *A61M 15/06* (2013.01); *H05B 3/0071* (2013.01); *A61M 2205/052* (2013.01)

(58) Field of Classification Search
CPC ... A24F 47/008; A61M 11/041; A61M 15/06; A61M 2205/052; H05B 3/0071
See application file for complete search history.

(56) References Cited

U.S. PATENT DOCUMENTS

| 5,499,636 A | 3/1996 | Baggett |
| 2012/0325227 A1 | 12/2012 | Robinson |

(Continued)

FOREIGN PATENT DOCUMENTS

| CN | 101975780 A | 2/2011 |
| CN | 103416852 A | 12/2013 |

(Continued)

OTHER PUBLICATIONS

Great Britain Search Report, Application No. GB1508405.6, dated Jun. 19, 2015, 5pages.

(Continued)

*Primary Examiner* — Joseph S Del Sole
*Assistant Examiner* — Jamel M Nelson
(74) *Attorney, Agent, or Firm* — Patterson Thuente Pedersen, P.A.

(57) ABSTRACT

In one example, an article is provided for use with an apparatus for generating an aerosol using an irradiative light source. The article has smokable material in combination with a transparent window through which light can pass. In another example, apparatus for generating an aerosol has an irradiative light source located in the apparatus. At least one optical component manipulates light emitted in use by the irradiative light source. A receptacle accommodates smokable material and receives light emitted in use by the irradiative light source. A transparent window is arranged between the receptacle and the at least one optical component. A combination of an apparatus for generating an aerosol and an article is also disclosed.

20 Claims, 5 Drawing Sheets

(51) Int. Cl.
*A61M 11/04* (2006.01)
*H05B 3/00* (2006.01)

(56) References Cited

U.S. PATENT DOCUMENTS

| | | |
|---|---|---|
| 2014/0060554 A1 | 3/2014 | Robert |
| 2014/0182608 A1* | 7/2014 | Egoyants .......... A61M 15/0091 131/328 |
| 2014/0311503 A1 | 10/2014 | Quming |
| 2014/0338680 A1 | 11/2014 | Ambramov |

FOREIGN PATENT DOCUMENTS

| | | |
|---|---|---|
| CN | 103610232 A | 3/2014 |
| CN | 203563690 U * | 4/2014 |
| CN | 203563690 U | 4/2014 |
| CN | 203646497 U | 6/2014 |
| CN | 104035527 | 9/2014 |
| CN | 204 177 782 U | 2/2015 |
| CN | 104522892 A | 4/2015 |
| CN | 204635080 U | 9/2015 |
| EP | 2462821 A1 | 6/2012 |
| JP | 2014-519850 | 8/2014 |
| JP | 2014-520542 | 8/2014 |
| KR | 20120074625 A | 7/2012 |
| KR | 20120103351 A | 9/2012 |
| RU | 121737 | 11/2012 |
| SU | 719560 A1 | 3/1980 |
| WO | WO98/17130 | 4/1998 |
| WO | WO 2013034458 A | 3/2013 |
| WO | WO 2013034459 A | 3/2013 |
| WO | WO 2013034460 A | 3/2013 |
| WO | WO 2014110119 | 7/2014 |
| WO | WO 2014110119 A1 | 7/2014 |
| WO | WO 2014140320 A | 9/2014 |
| WO | WO 2015066127 | 5/2015 |
| WO | WO 2016112579 | 7/2016 |
| WO | WO 2017/186944 | 11/2017 |
| WO | WO 2017/186946 | 11/2017 |

OTHER PUBLICATIONS

International Search Report, Application No. PCT/EP2016/060752, search completed Jul. 26, 2016 (dated Aug. 5, 2016), 5 pages.
Written Opinion, Application No. PCT/EP2016/060752, search completed Jul. 26, 2016 (dated Aug. 5, 2016), 6 pages.
Written Opinion, Application No. PCT/EP2016/060752, dated Apr. 3, 2017, 7 pages.
International Search Report, Application no. PCT/EP2017/060270, dated Aug. 23, 2017, 3 pages.
Great Britain Search Report, Application No. GB1607475.9, dated Oct. 20, 2016, 3 pages.
International Search Report, Application No. PCT/EP2014/060268, dated Aug. 23, 2017, 3 pages.
Great Britain Search Report, Application No. GB1607474.2, dated Oct. 20, 2016, 5 pages.
Korean Office Action, Application No. 10-2017-7033005, dated Nov. 6, 2018, 11 pages (18 pages with translation).
Japanese Office Action, Application No. 2017-55989, dated Nov. 27, 2018, 9 pages.
Application and File History for U.S. Appl. No. 16/096,874, filed Oct. 26, 2018, Inventor: Frobisher.
Application and File History for U.S. Appl. No. 16/096,863, filed Oct. 26, 2018, Inventor: Spencer.
English Translation of Russian Office Action, Application No. 20181377971, dated Oct. 16, 2019, 4 pages.
Chinese Office Action, Application No. 201680028124.8, dated Nov. 5, 2019, 26 pages.
Japanese Office Action, Application No. 2018-549157, dated Dec. 17, 2019, 10 pages.

* cited by examiner

ARTICLE AND APPARATUS FOR GENERATING AN AEROSOL

CROSS REFERENCE TO RELATED APPLICATION

The present application is a National Phase entry of PCT Application No. PCT/EP2016/060752, filed May 12, 2016, which claims priority from GB Patent Application No. 1508405.6, filed on May 15, 2015, each of which is hereby fully incorporated herein by reference.

TECHNICAL FIELD

The present disclosure relates to apparatus for generating an aerosol and to an article for use with apparatus for generating an aerosol.

BACKGROUND

Articles such as cigarettes, cigars and the like burn tobacco during use to create tobacco smoke. Attempts have been made to provide alternatives to these articles that burn tobacco by creating products that release compounds without burning. Examples of such products are so-called heat-not-burn products, also known as tobacco heating products or tobacco heating devices, which release compounds by heating, but not burning, the material. The material may be for example tobacco or other non-tobacco products or a combination, such as a blended mix, which may or may not contain nicotine. Similarly, there are also so-called e-cigarette devices, which typically vaporize a liquid, which may or may not contain nicotine.

SUMMARY

According to a first aspect of the present disclosure, there is provided an article for use with an apparatus for generating an aerosol using an irradiative light source, the article comprising: smokable material in combination with a transparent window through which light can pass, the article being constructed and arranged such that, when the article is received in apparatus comprising an irradiative light source for generating an aerosol using the irradiative light source, the transparent window is between the smokable material and the irradiative light source of the apparatus.

In an embodiment, the smokable material is affixed to the transparent window.

In an embodiment, the smokable material is affixed to the transparent window by at least one clip.

In an embodiment, the smokable material is removably affixed to the transparent window.

In an embodiment, the smokable material is adhered to the transparent window.

According to a second aspect of the present disclosure, there is provided an article for use with an apparatus for generating an aerosol using an irradiative light source, the article comprising: a retainer for retaining smokable material, the retainer having at least one transparent wall for covering at least a portion of smokable material retained in use by the retainer and through which irradiated light may pass to said smokable material to generate an aerosol.

The retainer with the transparent wall prevents or assists in preventing heated smokable material fouling the irradiative light source of the apparatus with which the article is used.

In an embodiment, the retainer has at least one wall that is opaque to the irradiated light of the light source of the apparatus with which the article is used. This can help protect certain components of the apparatus with which the article is used from light emitted by the irradiative light source.

In an embodiment, the retainer defines a chamber for receiving smokable material such that the transparent wall is arranged on one side of said smokable material and the opaque wall is arranged on the opposite side of said smokable material. In this example, the user can remove smokable material after use and insert fresh smokable material when needed. It may be noted that in use the smokable article may be left in situ in the apparatus for a number of smoking cycles prior to removal only once the smokable article has been fully depleted.

In an embodiment, the article comprises smokable material which is fixed to a wall of the retainer. In this example, the user can dispose of the article as a whole after use and use a new article, with fresh smokable material, when needed. This has a particular advantage that a new, clean transparent wall is used each time.

There may be provided, in combination, apparatus for generating an aerosol and an article according as described above, the apparatus comprising: an irradiative light source located in the apparatus; and at least one optical component for manipulating light emitted in use by the irradiative light source; the apparatus having a receptacle for accommodating the article and for receiving light emitted in use by the irradiative light source; the apparatus being constructed and arranged such that when the article is accommodated in the receptacle, light emitted in use by the irradiative light source can pass through the transparent wall of the retainer and such that the transparent wall of the retainer is arranged between the at least one optical component and smokable material retained in use by the retainer so as to prevent fouling of at least one optical component and the irradiative light source by aerosol produced in use by heating of smokable material using light emitted in use by the irradiative light source.

In an embodiment, the at least one optical component is a lens.

In an embodiment, the article is removably received in the receptacle. In an embodiment, smokable material is fixed to a wall of the retainer.

In an embodiment, the apparatus comprises control circuitry constructed and arranged so that the irradiative light source does not emit light while the article is being inserted into or removed from the receptacle.

In an embodiment, the article is fixed in the receptacle and smokable material is removably receivable in the chamber of the article.

In an embodiment, the apparatus comprises control circuitry constructed and arranged so that the irradiative light source does not emit light while the smokable material is being inserted into or removed from the chamber of the article.

According to a third aspect of the present disclosure, there is provided apparatus for generating an aerosol, the apparatus comprising: an irradiative light source located in the apparatus; at least one optical component for manipulating light emitted in use by the irradiative light source; a receptacle within the apparatus for accommodating smokable material and for receiving light emitted in use by the irradiative light source; and a transparent window arranged between the receptacle and the at least one optical component through which light emitted in use by the irradiative light source can pass into the receptacle and arranged so as to prevent aerosol produced in use by heating of said smokable material using light emitted in use by the irradiative light source fouling at least one of the at least one optical component and the irradiative light source.

In an embodiment, the at least one optical component is a lens.

In an embodiment, the apparatus comprises at least two sub housings, the sub housings being constructed and arranged to be openable by sliding one sub housing relative to the other sub housing so as to provide access to the receptacle.

In an embodiment, the apparatus comprises control circuitry constructed and arranged so that the irradiative light source does not emit light while the sub housings are being opened or are open to provide access to the receptacle.

In an embodiment, the apparatus comprises at least one air inlet and at least one airflow passage constructed and arranged so that in use air may enter the apparatus and be directed through the airflow passage over or through the receptacle for accommodating smokable material to an outlet of the apparatus without passing over at least one of the irradiative light source and the at least one optical component.

In an embodiment, the apparatus comprises smokable material accommodated within the receptacle, the smokable material being affixed to the transparent window, the smokable material and transparent window being removably received in the apparatus.

In an embodiment, the smokable material is removably affixed to the transparent window.

BRIEF DESCRIPTION OF THE DRAWINGS

Further features and advantages of the disclosure will become apparent from the following description of embodiments, given by way of example only, which is made with reference to the accompanying drawings.

DETAILED DESCRIPTION

As used herein, the term "smokable material" includes materials that provide volatilized components upon heating, typically in the form of an aerosol. "Smokable material" includes any tobacco-containing material and may, for example, include one or more of tobacco, tobacco derivatives, expanded tobacco, reconstituted tobacco or tobacco substitutes. "Smokable material" also may include other, non-tobacco, products, which, depending on the product, may or may not contain nicotine. "Smokable material" may for example be in the form of a solid, a liquid, a gel or a wax or the like. "Smokable material" may for example also be in a combination or a blend of materials.

Apparatus is known that heats smokable material to volatilize at least one component of the smokable material, typically to form an aerosol which can be inhaled, without burning or combusting the smokable material. Such apparatus is sometimes described as a "heat-not-burn" apparatus or a "tobacco heating product" or "tobacco heating device" or similar. Similarly, there are also so-called e-cigarette devices, which typically vaporize a smokable material in the form of a liquid, which may or may not contain nicotine. The smokable material may be in the form of or provided as part of a cartridge or cassette or the like which can be inserted into the apparatus. A heater for heating and volatilizing the smokable material may be provided as a "permanent" part of the apparatus or may be provided as part of the smoking article or consumable which is discarded and replaced after use. A "smoking article" in this context is a device or article or other component that includes or contains in use the smokable material, which in use is heated to volatilize the smokable material, and optionally other components.

Figure 1:
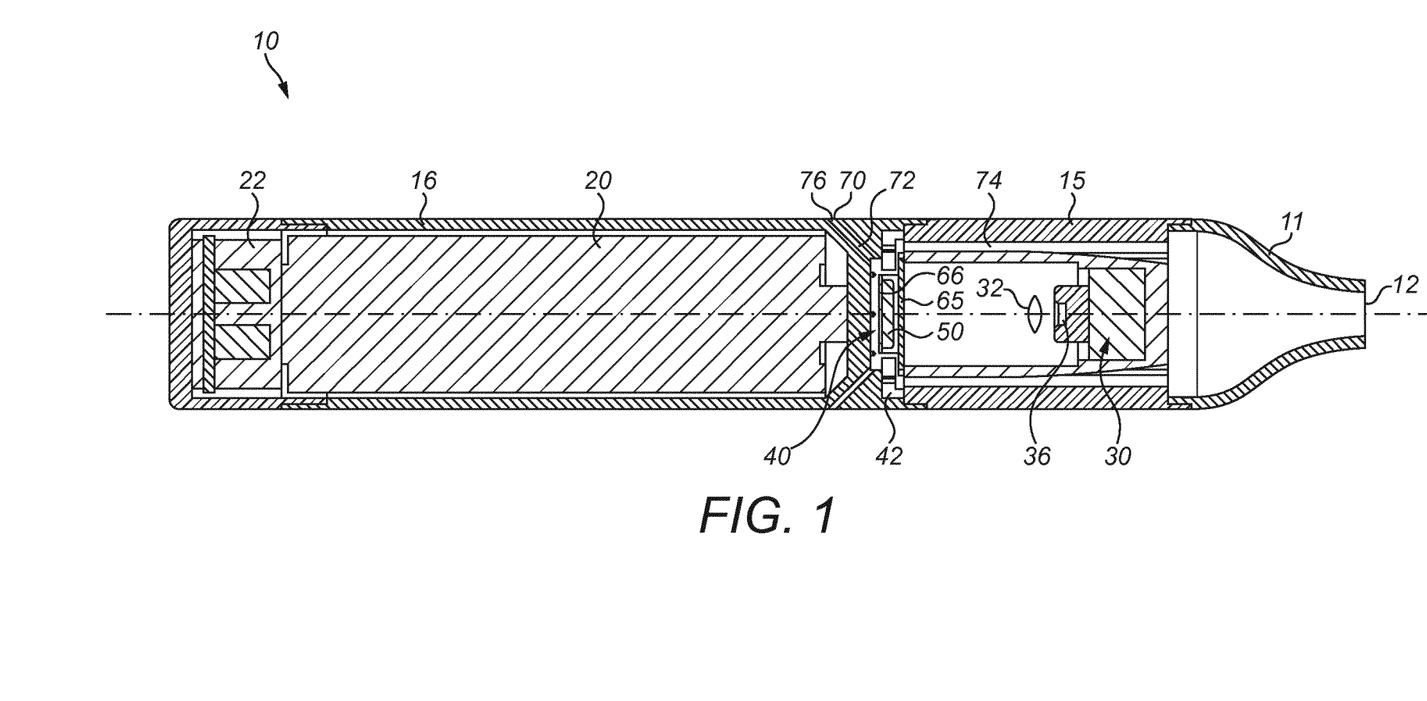
FIG. 1 shows a longitudinal schematic cross-sectional view of an example of an apparatus arranged to heat smokable material.

Referring to FIG. 1, there is shown a longitudinal schematic cross-sectional view of an example of an apparatus 10 arranged to heat smokable material to volatilize at least one component of said smokable material, typically to form an aerosol which can be inhaled, without burning the smokable material. The apparatus 10 in this example is generally an elongate cylinder of circular cross-section. The apparatus 10 has a mouthpiece 11 with an opening 12.

Contained within the apparatus 10 there is a power source 20 and electrical control circuitry 22 to power and control the functioning of the apparatus 10 respectively. The power source 20 may be a battery, which may be a rechargeable battery or a non-rechargeable battery. Examples of suitable batteries include for example a lithium-ion battery, a nickel battery (such as a nickel-cadmium battery), an alkaline battery and/or the like. Alternatively, the power source 20 could be any suitable chemical or electrical source of energy, including for example a capacitor. Contained within the apparatus 10 there is also an irradiative light source 30 for irradiating smokable material contained in use in the apparatus 10. The apparatus 10 also contains at least one optical component for manipulating light emitted in use by the irradiative light source 30. The at least one optical component for manipulating light may be a mirror, a beam splitter, a collimator or any other optical component that may enable the manipulation of light. In the example shown, there is a lens 32 for manipulating light emitted in use by the irradiative light source 30 is also contained within the apparatus 10. The manipulation of the light by the lens 32 may include one or more of focusing the light and directing/bending the light. The apparatus 10 further has a receptacle 40 for accommodating smokable material 50 and for receiving light emitted in use by the irradiative light source 30.

The irradiative light source 30 produces light which is used to heat the smokable material 50 contained in use in the receptacle 40. The term "light" here should normally be interpreted broadly, and includes for example any of infrared, visible and ultraviolet light. Suitable wavelengths of light include those from 150 nm to 1 mm. The light may be laser light. For example, the irradiative light source 30 may include a laser diode 36 for generating laser light. The laser diode 36 may be arranged in and supported by a laser mount 38.

The apparatus 10 in use heats smokable material 50 received or located within the receptacle 40 using light emitted by the irradiative light source 30. The light emitted by the irradiative light source 30 is manipulated, i.e. focused and/or directed, by the lens 32 so as to strike the smokable material 50. The light is absorbed by the smokable material 50 such that heating and volatilization of the smokable material 50 occurs. The apparatus 10 further contains a transparent wall or window 65 arranged between the lens 32 and the receptacle 40. The transparent window 65 allows light to pass but prevents or assists in preventing material produced in use by heating of smokable material 50 fouling at least one and preferably both of the lens 32 and the irradiative light source 30. It should be noted that the transparent window 65 as a minimum needs only to be transparent to the wavelength(s) of light that is emitted by the irradiative light source 30, and indeed only sufficiently transparent to let sufficient light through to heat the smokable material, and may be opaque or transparent to other wavelengths. It will be understood that the transparent window 65 merely provides a protective window function, and does not provide a lensing function which is performed by the lens 32. The transparent window 65 may be rigid or substantially rigid. Suitable materials for the transparent window 65 include for example glass, of which a number of different types are suitable in this application, or plastics, of which again a number of different types are suitable in this application, such as a substantially rigid transparent film window. The transparent window 65 may for example have a thin film coating to ensure a suitable level of light transmission. Anti-bloom coatings for example may increase the transmission of light through the window. In another example self-cleaning coatings may ensure a consistent transmission of light through the window over periods of use. In yet another example, the transparent window 65 may not be rigid, and may for example be in the form of a non-rigid film or the like.

Figure 2:
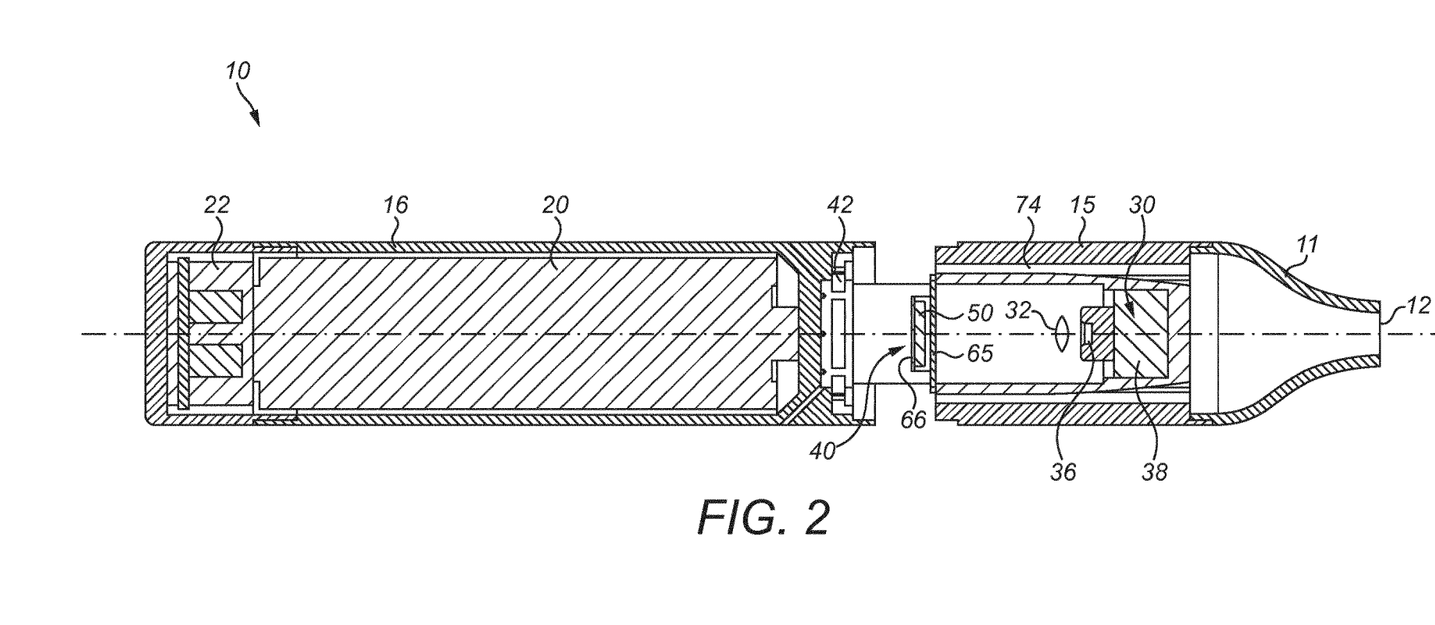
FIG. 2 shows a longitudinal schematic cross-sectional view of the apparatus of FIG. 1 with sub housings pulled apart.

Various arrangements for allowing smokable material to be inserted into and removed from the apparatus 10 are possible. For example, the apparatus 10 may have a sliding or hinged door (not shown) to allow access to the interior of the apparatus. In another example, the apparatus 10 may be formed of at least two sub housings; in the specific example shown in FIG. 1 the two sub housings are a laser diode housing 15, which contains the lens 32, laser diode 36 and laser mount 38, and a battery/control housing 16, which contains the power source 20 and electrical control circuitry 22. In the specific example shown schematically in FIG. 1, the laser diode housing 15 and the battery/control housing 16 are arranged to be openable to provide access to the receptacle 40. This may be for example through a sliding arrangement whereby one sub housing can be slid apart from the other sub housing, or for example by unscrewing one sub housing from the other sub housing. Before use, the user is able to open the sub housings and insert smokable material 50 into the receptacle 40 and then close the sub housings. Likewise, after use, the user is able to remove depleted smokable material 50 from the receptacle 40. An example of this is shown schematically in FIG. 2, which shows the battery/control housing 16 having been pulled slightly apart from the laser diode housing 15 to allow access to the receptacle 40 such that smokable material 50 can be inserted and removed. The sub housings 15, 16 may have a seal over the break in the sub housings so as to ensure a tight fit when the sub housings 15, 16 are closed. Such a seal may take the form of, for example, an O-ring or by mating surface interference or the like.

The apparatus 10 has at least one air inlet orifice 70 in the surface of the apparatus 10 to admit air into the apparatus 10 in use. In the example shown, the apparatus 10 has 8 air inlet orifices 70 located circumferentially around the apparatus 10 and close to the receptacle 40 for the smokable material 50. The apparatus 10 further has inlet air flow passages 72 so that in use incoming air can flow from the air inlet orifices 70, through the inlet air flow passages 72 and through or over the receptacle 40. The apparatus 10 further has outlet air flow passages 74 which are arranged so that air that has passed through or over the receptacle 40 can flow towards the mouthpiece 11 and exit the apparatus 10 through the opening 12 of the mouthpiece 11.

Figure 3:
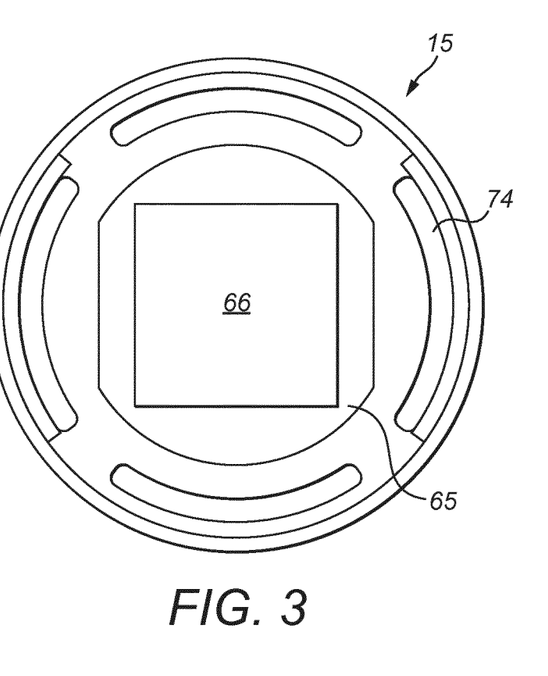
FIG. 3 shows an end view of a laser diode housing of the apparatus of FIGS. 1 and 2.

In the example shown in FIG. 1, the inlet air flow passages 72 are each in the form of a hollow channel which leads from the respective air inlet orifices 70 in the apparatus 10 towards the receptacle 40. In use, air enters the air inlet orifices 70 and then through the inlet air flow passages 72 and then enters or flows over the receptacle 40 to entrain volatilized material produced when the smokable material 50 is heated. The air with entrained volatilized material then flows into the outlet air flow passages 74 after flowing through or over the receptacle 40. The transparent wall or window 65 is arranged against the laser diode housing 15 so as to prevent air and volatilized material flowing into the interior of the laser diode housing 15 and over the irradiative light source 30 and lens 32. Referring to the end view of the laser diode housing 15 shown in FIG. 3, in this example the outlet air flow passages 74 take the form of arcuate channels through the laser diode housing 15 and arranged around the longitudinal axis of the laser diode housing 15, with four outlet airflow passages 74 being provided in this particular example. Preventing the air with entrained volatilized material from flowing into the interior of the laser diode housing 15 keeps material away from the lens 32 and laser diode 36 and thus keeps the lens 32 and laser diode 36 clean and free of contaminants, which is important to ensure a long lifetime for the apparatus 10 and the irradiative light source 30 and optical components.

In an example, the or each air inlet orifice 70 is covered by a valve 76. The valve 76 selectively enables the entrance of air into the apparatus 10 when the apparatus 10 is in use. In an example the valve 76 is a non-return rubber slit valve which opens when a user is drawing on the mouthpiece 11 and ensures air cannot enter the apparatus 10 otherwise.

In some examples, smokable material 50 on its own, as a discrete item, can be inserted into and removed from the receptacle 40 in the apparatus 10. In other examples, smokable material 50 may be inserted into and removed from the receptacle 40 in the apparatus 10 as part of a separate article which can act as a carrier or mount for the smokable material 50. In this case, the apparatus 10 has internal retaining walls 42 which face each other to define a channel which receives the separate article with smokable material.

Figure 4:
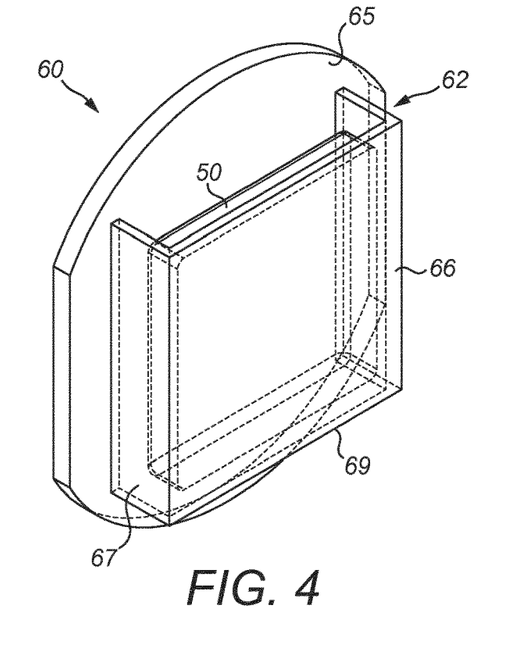
FIG. 4 shows a schematic perspective view of an example of an article that is suitable for use with an apparatus for generating an aerosol.
Figure 5:
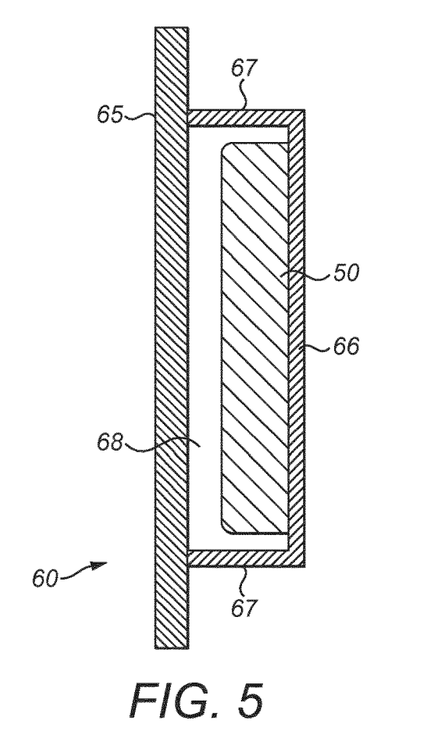
FIG. 5 shows a schematic longitudinal cross-sectional view of the article of FIG. 4.

Referring to FIGS. 4 and 5, there is shown a schematic perspective view and a longitudinal cross-sectional view of an example of an article 60 that is particularly suitable for use with an apparatus for generating an aerosol using an irradiative light source and which can act as a carrier or mount for the smokable material. The apparatus may be apparatus 10 as described above with reference to FIGS. 1 to 3, though other arrangements for the apparatus are possible.

The article 60 as shown in FIGS. 4 and 5 has or provides a retainer 62 for retaining smokable material. The retainer 62 has at least one transparent wall or window 65 that is transparent to the irradiated light of the light source 30 of the apparatus 10 with which the article 60 is used. The at least one transparent wall 65 is for covering at least a portion of the smokable material 50 retained in use by the retainer 62.

The transparent wall 65 allows irradiated light to pass through the transparent wall 65 and to the smokable material 50. The transparent part may be a small transparent window in an otherwise opaque wall or, as shown in this example, may be a complete transparent wall 65. It should be noted that the transparent wall 65 as a minimum needs only to be transparent to the wavelength(s) of light that is emitted by the irradiative light source 30 of the apparatus 10 with which the article 60 is used, and indeed only sufficiently transparent to let sufficient light through to heat the smokable material, and may be opaque or transparent to other wavelengths. Suitable materials for the transparent wall or window 65 include for example glass, of which a number of different types are suitable in this application, or plastics, of which again a number of different types are suitable in this application.

The retainer 62 has at least one wall 66 that is opaque to the irradiated light of the light source 30 of the apparatus 10 with which the article 60 is used. The retainer 62 defines a chamber 68 for receiving smokable material 50. In this example, the chamber 68 is formed by at least the transparent wall 65 arranged on one side of the smokable material 50 and the opaque wall 66 arranged on the opposite side of the smokable material 50. Depending on the shape of the chamber 68, there may be other walls. Other walls, if present, such as side walls 67 and a bottom wall 69, are also opaque in this example. It should be noted that the rear opaque wall 66 as a minimum needs only to be opaque to the wavelength(s) of light that is emitted by the irradiative light source 30, and may be opaque or transparent to other wavelengths. Suitable materials for the opaque wall 66 include for example metal, certain plastics, etc.

The opaque walls 66, 67, 69 in some examples ensure that the light from the irradiative light source 30 of the apparatus 10 with which the article 60 is used does not pass through to components of the apparatus 10 that are located behind the article 60 in use, including for example the power source 20 and electrical control circuitry 22 of the apparatus 10. The chamber 68 is open or has an opening at one side (the upper side in FIG. 4) so that volatilized material produced when the smokable material 50 is heated can escape the chamber 68 and be entrained by air flowing through the apparatus 10 with which the article 60 is used.

In one example, the smokable material 50 is removably received in the chamber 68 and the user is able to insert smokable material 50 into the chamber 68 prior to use of the article 60 and remove depleted smokable material from the chamber 68 after use of the article 60. In another example, the smokable material 50 may be fixed to a wall of the retainer 62, such as by use of an adhesive or some other arrangement; in the example shown the smokable material 50 is fixed to the rear wall 66 of the retainer 62. In an example, the smokable material 50 is affixed to the transparent window 65. In an example, the smokable material 50 is affixed to the transparent window 65 by at least one clip. In an example, the smokable material 50 is removably affixed to the transparent window 65, for example by the use of at least one clip. There may be for example two such clips. The or each clip may for example be part of the transparent window 65 or a separate item. In yet another example, the smokable material 50 may be adhered to the transparent window, for example by the use of a suitable glue. In this example the smokable material 50 is permanently fixed to the window. Also in this example, after use the user may remove both the article 60 and depleted smokable material as a whole from the apparatus 10 and replace them with a new article 60 with fresh smokable material 50. An advantage of replacing the article 60 as a whole after the smokable material 50 has been depleted is that the transparent wall 65 of the new article 60 will be clean. A clean transparent wall 65 has an increased transmission of the light through it compared to a wall that has had volatilized smokable material repeatedly flow over it. The increase in transmission will improve the efficiency of the apparatus 10 and therefore use less power in generating an aerosol. This means the apparatus 10 is able to work for longer using a particular power source, or require fewer charges per period of use. Inserting a new article 60 each time the smokable material 50 depletes will also enable a user to more easily avoid contact with the smokable material 50.

Figure 6:
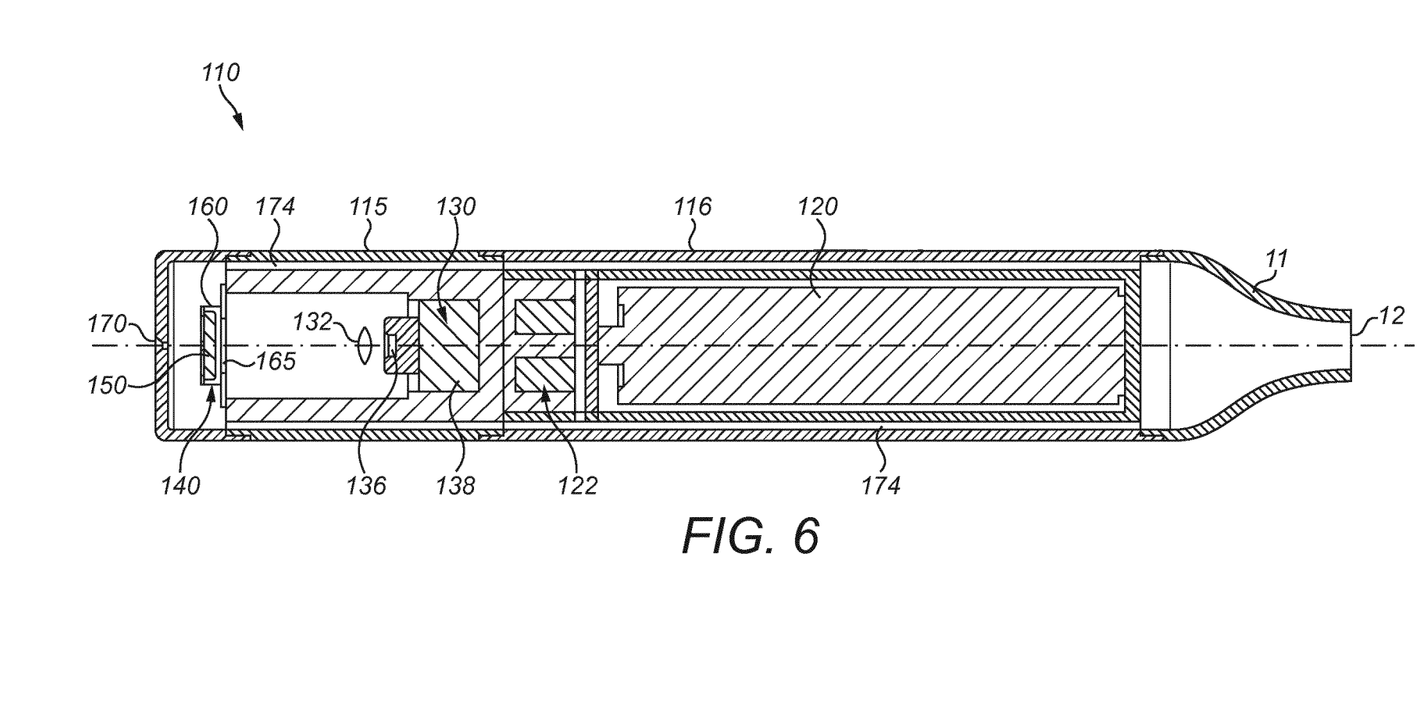
FIG. 6 shows a longitudinal schematic cross-sectional view of another example of an apparatus arranged to heat smokable material.

Referring to FIG. 6, there is shown a longitudinal schematic cross-sectional view of another example of an apparatus 110 arranged to heat smokable material 150 to volatilize at least one component of said smokable material 150, typically to form an aerosol which can be inhaled, without burning the smokable material 150. The apparatus 110 of FIG. 6 is generally similar to the example of an apparatus 10 discussed above with reference to FIGS. 1 to 3, and corresponding parts have the same reference numerals increased by 100. A detailed description of the same or corresponding parts will not be given here for the sake of brevity, it being understood that the description given above is applicable to this example. Nevertheless, the apparatus 110 of FIG. 6 has mouthpiece 111 at one end with an opening 112, a power source 120 and electrical control circuitry 122, an irradiative light source 130 and a lens 132. The irradiative light source 130 in this example includes a laser diode 136 for generating laser light (though, as above, other light sources to produce non-laser light may be used in some circumstances). The laser diode 136 is arranged in and supported by a laser mount 138. The apparatus 110 has a receptacle 140 for receiving smokable material 150, either as a discrete item or as part of a separate article which can act as a carrier or mount for the smokable material 150, again as discussed above. A transparent wall or window 165 separates the smokable material 150 from the laser diode 136 and lens 132. The transparent wall or window 165 may be fixed in the apparatus 110 or may be part of a separate article which can act as a carrier or mount for the smokable material 150 and which is inserted into and removed from the apparatus 110 a whole.

In the apparatus 110 of FIG. 6, the power source 120 and electrical control circuitry 122 are generally towards the proximal or mouth end of the apparatus 110 and the irradiative light source 130 is generally towards the opposite, distal end. An air inlet orifice 170 is provided at the distal end of the apparatus 110. Plural air inlet orifices 170 may be provided. Incoming air entering the air inlet orifice(s) 170 flows through or over the receptacle 140 to entrain volatilized material produced when the smokable material 150 is heated. The air with entrained volatilized material then flows into the one or more outlet air flow passages 174 after flowing through or over the receptacle 140. The outlet air flow passages 174 direct the air flow along the length of the apparatus 110 towards the mouthpiece 111. Similarly to the example of the laser diode housing 15 discussed above with particular reference to FIG. 3, in this example of the apparatus 110 the outlet air flow passages 174 may be in the form of arcuate channels through the laser diode housing 115 and the battery/control housing 116. The relatively long air flow path in this example of the apparatus 110 compared to the example shown in FIGS. 1 to 3 enables the air flow to cool more before exiting the apparatus 110.

The various embodiments described herein are presented only to assist in understanding and teaching the claimed features. These embodiments are provided as a representative sample of embodiments only, and are not exhaustive and/or exclusive. It is to be understood that advantages, embodiments, examples, functions, features, structures, and/or other aspects described herein are not to be considered limitations on the scope of the invention as defined by the claims or limitations on equivalents to the claims, and that other embodiments may be utilized and modifications may be made without departing from the scope of the claimed invention. Various embodiments of the invention may suitably comprise, consist of, or consist essentially of, appropriate combinations of the disclosed elements, components, features, parts, steps, means, etc., other than those specifically described herein. In addition, this disclosure may include other inventions not presently claimed, but which may be claimed in future.

The invention claimed is:

1. An article for use with an apparatus for generating an aerosol using an irradiative light source contained within a housing of the apparatus, the apparatus having a receptacle for receiving light emitted in use by the irradiative light source to generate the aerosol in the receptacle, the article constructed and arranged to be accommodated in the receptacle, the article comprising:

a smokable material in combination with a solid transparent window through which light can pass, the article being constructed and arranged such that, when the article is received in the receptacle of the apparatus comprising the irradiative light source for generating the aerosol using the irradiative light source, the solid transparent window is between the smokable material and the irradiative light source of the apparatus to prevent the aerosol produced in use in the receptacle by heating of the smokable material flowing into the housing and over the irradiative light source and the at least one optical component, so as to prevent fouling of the irradiative light source by the aerosol.

2. The article according to claim 1, wherein the smokable material is adhered to the solid transparent window.

3. The article according to claim 1, wherein the smokable material is affixed to the solid transparent window.

4. The article according to claim 3, wherein the smokable material is affixed to the solid transparent window by at least one clip.

5. The article according to claim 3, wherein the smokable material is removably affixed to the solid transparent window.

6. The article for use with an apparatus for generating an aerosol using an irradiative light source, the apparatus having a receptacle for receiving light emitted in use by the irradiative light source to generate the aerosol in the receptacle, the article constructed and arranged to be accommodated in the receptacle, the article comprising:

a retainer for retaining a smokable material, the retainer having at least one solid transparent wall or window for covering at least a portion of smokable material retained in use by the retainer and through which irradiated light may pass to the smokable material when the article is received in the receptacle to generate the aerosol in the receptacle, wherein the retainer is constructed and arranged such that, when the article is accommodated in the receptacle, the solid transparent wall of the retainer is arranged between the irradiative light source and the smokable material retained in use by the retainer.

7. The article according to claim 6, comprising smokable material which is fixed to a wall of the retainer.

8. The article according to claim 6, wherein the retainer has at least one wall that is opaque to the irradiated light of the light source of the apparatus with which the article is used.

9. The article according to claim 8, wherein the retainer defines a chamber for receiving smokable material such that the solid transparent wall is arranged on one side of said smokable material and the opaque wall is arranged on the opposite side of said smokable material.

10. The article according to claim 9, comprising smokable material removably received in the chamber.

11. A system comprising:

an apparatus for generating an aerosol; and an article, the apparatus comprising:

an irradiative light source located in the apparatus; and at least one optical component for manipulating light emitted in use by the irradiative light source, the apparatus having a receptacle for accommodating the article and for receiving light emitted in use by the irradiative light source to generate the aerosol in the receptacle;

the article constructed and arranged to be accommodated in the receptacle, the article comprising:

a retainer for retaining a smokable material, the retainer having at least one solid transparent wall or window for covering at least a portion of the smokable material retained in use by the retainer and through which irradiated light may pass to the smokable material when the article is received in the receptacle to generate the aerosol in the receptacle, wherein the retainer is constructed and arranged such that, when the article is accommodated in the receptacle, the solid transparent wall or window of the retainer is arranged between the irradiative light source and the smokable material retained in use by the retainer, wherein the apparatus is constructed and arranged such that when the article is accommodated in the receptacle, light emitted in use by the irradiative light source can pass through the solid transparent wall or window of the retainer and such that the solid transparent wall or window of the retainer is arranged between the at least one optical component and the smokable material retained in use by the retainer so as to prevent fouling of at least one of the at least one optical component or the irradiative light source by the aerosol produced in use in the receptacle by heating of the smokable material using light emitted in use by the irradiative light source.

12. The system according to claim 11, wherein the at least one optical component is a lens.

13. The system according to claim 11, wherein the article is fixed in the receptacle and the smokable material is removably receivable in a chamber of the article.

14. The system according to claim 11, wherein the article is removably received in the receptacle.

15. The system according to claim 14, comprising smokable material that is at least one of removably received in the chamber or fixed to a wall of the retainer, wherein both the article and the smokable material are removably received in the receptacle as a whole.

16. The system according to claim 14, wherein the apparatus comprises a control circuitry constructed and arranged so that the irradiative light source does not emit light while the article is being inserted into or removed from the receptacle.

17. An apparatus for generating an aerosol, the apparatus comprising:
    an irradiative light source located in a housing in the apparatus;
    at least one optical component for manipulating light emitted in use by the irradiative light source;
    a receptacle within the apparatus for accommodating a smokable material and for receiving light emitted in use by the irradiative light source; and
    a solid transparent window arranged between the receptacle and the at least one optical component through which light emitted in use by the irradiative light source can pass into the receptacle and arranged so as to prevent aerosol produced in use by heating of the smokable material using light emitted in use by the irradiative light source flowing into the housing and over the irradiative light source and the at least one optical component to as to prevent the aerosol fouling at least one of the at least one optical component or the irradiative light source.

18. The apparatus-according to claim 17, wherein the at least one optical component is a lens.

19. The apparatus-according to claim 17, wherein the apparatus comprises at least two sub housings, the sub housings being constructed and arranged to be openable by sliding one sub housing relative to the other sub housing so as to provide access to the receptacle.

20. The apparatus according to claim 17, comprising at least one air inlet and at least one airflow passage constructed and arranged so that in use air may enter the apparatus and be directed through the airflow passage over or through the receptacle for accommodating smokable material to an outlet of the apparatus without passing over at least one of the irradiative light source or the at least one optical component.

* * * * *